United States Patent
Boss et al.

(10) Patent No.: US 10,192,420 B2
(45) Date of Patent: Jan. 29, 2019

(54) MONITORING DEVICE AND MONITORING SYSTEM

(71) Applicant: MSA Europe GmbH, Jona (CH)

(72) Inventors: Jürgen Boss, Berlin (DE); Julian Möller, Berlin (DE); Alexander Fronzke, Berlin (DE)

(73) Assignee: MSA EUROPE GMBH, Jona (CH)

( * ) Notice: Subject to any disclaimer, the term of this patent is extended or adjusted under 35 U.S.C. 154(b) by 0 days.

(21) Appl. No.: 15/128,653

(22) PCT Filed: Mar. 20, 2015

(86) PCT No.: PCT/EP2015/055964
§ 371 (c)(1),
(2) Date: Sep. 23, 2016

(87) PCT Pub. No.: WO2015/144589
PCT Pub. Date: Oct. 1, 2015

(65) Prior Publication Data
US 2017/0109993 A1    Apr. 20, 2017

(30) Foreign Application Priority Data
Mar. 25, 2014  (DE) .......................... 10 2014 104 131

(51) Int. Cl.
*G08B 21/04* (2006.01)
*H04W 4/80* (2018.01)
(Continued)

(52) U.S. Cl.
CPC ........ *G08B 21/0453* (2013.01); *A61B 5/0015* (2013.01); *A61B 5/0022* (2013.01);
(Continued)

(58) Field of Classification Search
CPC .............. G08B 21/0453; G08B 25/016; A61B 5/0015; A61B 5/01; A61B 5/02055;
(Continued)

(56) References Cited

U.S. PATENT DOCUMENTS 5,392,771 A    2/1995  Mock et al.
5,704,367 A *  1/1998  Ishikawa ................ A61B 5/113
                                                        600/473
(Continued)

FOREIGN PATENT DOCUMENTS

DE    4033292 A1   4/1992
WO    0108752 A1   2/2001
(Continued)

OTHER PUBLICATIONS

Lee et al. "Implementation of Accelerometer Sensor Module and Fall Detection Monitoring System based on Wireless Sensor Network." Proceedings of the 29th Annual Conference of the IEEE Engineering in Medicine and Biological Society; 2007; pp. 2315-2318. (Accessed at www.intechopen.com).

*Primary Examiner* — Nay Tun
(74) *Attorney, Agent, or Firm* — The Webb Law Firm (57) ABSTRACT

A monitoring device having at least one data processing unit, at least one transmitter and/or receiver unit, at least one acceleration sensor, and can be connected to at least one sensor for recording measured values, wherein the data processing unit has at least two operating modes, including a "basic mode" and a "base station mode", wherein: in the "basic mode", the measured values of the acceleration sensor and/or of the at least one sensor are monitored, in the "base station mode", the measured values can be processed by at least one other but compatible monitoring device in the "basic mode". The invention also relates to a monitoring system.

18 Claims, 7 Drawing Sheets

(51) Int. Cl.
  *A61B 5/0205* (2006.01)
  *A61B 5/01* (2006.01)
  *A61B 5/11* (2006.01)
  *A61B 5/1455* (2006.01)
  *G08B 25/01* (2006.01)
  *G06F 19/00* (2018.01)
  *G16H 40/67* (2018.01)
  *H04W 4/90* (2018.01)
  *H04L 29/08* (2006.01)
  *A61B 5/00* (2006.01)
  *H04W 4/021* (2018.01)
  *A61B 5/024* (2006.01)

(52) U.S. Cl.
  CPC ............ *A61B 5/01* (2013.01); *A61B 5/02055* (2013.01); *A61B 5/1112* (2013.01); *A61B 5/14551* (2013.01); *A61B 5/6802* (2013.01); *A61B 5/742* (2013.01); *G06F 19/00* (2013.01); *G08B 21/0446* (2013.01); *G08B 25/016* (2013.01); *G16H 40/67* (2018.01); *H04W 4/80* (2018.02); *A61B 5/024* (2013.01); *A61B 5/6801* (2013.01); *A61B 2503/20* (2013.01); *A61B 2560/0242* (2013.01); *A61B 2562/0219* (2013.01); *G08B 21/0476* (2013.01); *H04L 67/125* (2013.01); *H04W 4/021* (2013.01); *H04W 4/90* (2018.02)

(58) Field of Classification Search
  CPC . A61B 5/1112; A61B 5/14551; A61B 5/6802; A61B 5/742; A61B 5/024; A61B 2560/0242; A61B 2562/0219
  See application file for complete search history.

(56) References Cited

U.S. PATENT DOCUMENTS

| | | |
|---|---|---|
| 6,522,531 B1 | 2/2003 | Quintana et al. |
| 2004/0131498 A1 | 7/2004 | Kuutti |
| 2006/0020981 A1* | 1/2006 | Paik ............... H04N 5/44513 725/81 |
| 2006/0125630 A1 | 6/2006 | Parkulo |
| 2008/0284589 A1 | 11/2008 | Parkulo |
| 2009/0069642 A1 | 3/2009 | Gao et al. |
| 2009/0076344 A1* | 3/2009 | Libbus ............. A61B 5/02055 600/301 |
| 2012/0274554 A1* | 11/2012 | Kinoshita ........... A61B 5/1118 345/156 |
| 2013/0057696 A1 | 3/2013 | Felt et al. |
| 2014/0139616 A1* | 5/2014 | Pinter ............... A61B 5/0008 348/14.08 |
| 2014/0206977 A1* | 7/2014 | Bahney ............. A61B 5/6833 600/391 |
| 2014/0320311 A1* | 10/2014 | Huang ............... H04W 4/006 340/870.09 |
| 2015/0150505 A1* | 6/2015 | Kaskoun ........... A61B 5/6833 600/300 |
| 2016/0028869 A1* | 1/2016 | Bhatt ............... H04M 1/7253 455/41.2 |

FOREIGN PATENT DOCUMENTS

| | | |
|---|---|---|
| WO | 2013109577 A2 | 7/2013 |
| WO | 2013178869 A1 | 12/2013 |

\* cited by examiner

MONITORING DEVICE AND MONITORING SYSTEM

CROSS-REFERENCE TO RELATED APPLICATIONS

This application is the United States national phase of International Application No. PCT/EP2015/055964 filed Mar. 20, 2015, and claims priority to German Patent Application No. 10 2014 104 131.3 filed on Mar. 25, 2014, the disclosures of which are hereby incorporated in their entirety by reference.

BACKGROUND OF THE, INVENTION

Field of the Invention

The invention relates to a monitoring device and system.

Description of Related Art

In various sectors of working life, activities are performed that are hazardous to the health of persons. These sectors include, for example, the work of firemen, industrial divers, rescue teams, emergency teams in disaster zones or in industrial installations. In order to minimize the risks for these groups of persons, monitoring devices are used.

The monitoring devices, in the form of gas sensors, for example, detect a risk situation for a person early and they communicate this to the person or also to another monitoring person or to a monitoring system. Therefore it is possible to initiate rescue operations if necessary.

In WO 01/08752 A1, a corresponding system is described, wherein a person with a separate base station is a precondition. The base station is implemented as a PC, a laptop or a tablet.

SUMMARY OF THE INVENTION

In summary, one embodiment provides a monitoring device to be worn on a person, wherein the monitoring device comprises at least one data processing unit, at least one transmitter and/or receiver unit, as well as at least one acceleration sensor; moreover the monitoring device can be connected to at least one sensor for recording measured values, characterized in that the data processing unit (2) has, as operating modes, at least a "basic mode" (G) and a "base station mode" (B), wherein: a) in the "basic mode" (G), the measured values of the acceleration sensor (2) and/or of the at least one sensor (20) are monitored, said measured values being measured on the person, in the surroundings of the person and/or on the equipment of the person, b) in the "base station mode" (B), the measured values can be processed by at least one other but compatible monitoring device (1) in the "basic mode" (G).

Another embodiment provides a monitoring device to be worn by a person, wherein the monitoring device comprises at least one data processing unit, at least one transmitter and/or receiver unit, as well as at least one acceleration sensor, and moreover the monitoring device can be connected to at least one sensor for recording measured values, characterized in that a display (5) can be controlled, in particular switched on and off, by a signal of the at least one acceleration sensor (4).

An additional embodiment provides a mobile monitoring device, comprising: at least one transmitter; at least one receiver; at least one sensor; and at least one processing unit in operative connection with the at least one transmitter, the at least one receiver, and the at least one sensor; wherein at least one processing unit sets the mobile monitoring device to one of a basic mode and a base station mode according to a setting.

Another embodiment provides a monitoring system, comprising: a plurality of mobile monitoring devices; one of the plurality of mobile monitoring devices being set to a base station mode; each remaining device of the plurality of mobile monitoring devices being set to a basic mode; the one of the plurality of mobile monitoring devices set to the base station mode receiving data from and issuing commands to each remaining device of the plurality of mobile monitoring devices set to the basic mode; wherein each remaining device of the plurality of mobile monitoring devices is configurable to be set to the base station mode; and wherein the one of the plurality of mobile monitoring devices set to the base station is thereafter set to the basic mode.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION OF THE INVENTION

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of certain example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment Furthermore, the described features, structures, or characteristics may be combined in any suitable manner in one or more embodiments. In the following description, numerous specific details are provided to give a thorough understanding of certain embodiments. One skilled in the relevant art will recognize, however, that the various embodiments can be practiced without one or more of the specific details, or with other methods, components, materials, etc. In other instances, well known structures, materials, or operations are not shown or described in detail to avoid obfuscation. The following description is intended only by way of example, and simply illustrates certain example embodiments.

In WO 01/08752 A1, a system is described wherein a person with a separate base station is a precondition. Since the monitoring person needs a base station for the person to be monitored, two different apparatus types have to be procured, maintained and operated. Due to the heavy weight and the major form factor of a separate base station, the person as a rule needs both hands in order to operate the base station.

Therefore, there is a demand for efficient monitoring possibilities.

The problem is solved by a monitoring device having the features of claim 1.

According to the invention, the monitoring device to be worn on a person comprises at least one transmitter and/or receiver unit, as well as at least one acceleration sensor. Furthermore, it can be connected to at least one sensor for recording measured values, and it comprises at least one data processing unit, which, as operating modes, has at least a "basic mode" and a "base station mode." In the "basic mode" the measured values of the acceleration sensor and/or of the at least one sensor are monitored, said measured values being measured on the person, in the surroundings of the person and/or on the equipment of the person. In the "base station mode," the measured values of at least one additional but compatible monitoring device are processed in the "basic mode." As a result of the use of this monitoring device, no separate base station needs to be used. This allows the monitoring person greater freedom of operation and increased flexibility. In addition, there is also reduced maintenance and operating expenditure, because it is no longer necessary to procure and operate two different apparatuses.

Frequently, a display is a component that has a relatively high current consumption. The current consumption can be reduced if the current supply of the display depends on the measured values of the acceleration sensor, i.e., a distinction is made between a usage situation and a non-usage situation. If, for example, the acceleration sensor measures that the monitoring device is suspended from the body of the person, which can be determined, for example, by a detection of suspension (downward-pointing terrestrial gravity vector), the display is automatically switched off or dimmed, for example. On the other hand, if the monitoring device is moved out of this position, this is also detected by the acceleration sensors, so that the display can be switched automatically to the normal mode. The operation is thereby considerably simplified for the person who takes the monitoring device with himself/herself. In special cases, for example, in the case of an alarm, the actuation can be changed, so that the display is also activated in a non-usage situation.

Another problem is solved by a monitoring device having the features of claim 3. Here, a display can be controlled, in particular switched on and off, by a signal of the at least one acceleration sensor. Displays use a considerable amount of energy, so that the efficient control of the energy consumption is important. For example, the at least one acceleration sensor can register when the monitoring device has been moved by the user from a suspended storage position into a horizontal observation position. This registered movement is then used in order to switch on the display. If the user brings the monitoring device again into the suspended storage position, the display is switched off again. In principle, it is also possible to capture other, in particular more complex, motion patterns as well with the at least one acceleration sensor, in order to actuate the display. The features of the monitoring devices according to claims 1 and 2 can also be combined with one another.

In an embodiment, the monitoring device has a bidirectional communication unit, a pager function and/or a repeater function. Due to the bidirectional communication, a complete, reciprocal communication can be carried out. A pager is suitable for transmitting short messages, dates and/or signals from a transmitter to a receiver, which can be useful particularly in emergency situations. In this manner it is possible, for example, for the operator of a base station to be notified that a warning or alarm status has occurred. A repeater makes it possible to increase the range, which is particularly helpful in the case of spatially larger deployment areas.

In an embodiment, it is possible to set, i.e., to activate, both the "basic mode" and also the "base station mode" in one and the same monitoring device. As a result, monitoring devices can be used as a personal equipment item, as needed. However, it is also possible to use a monitoring device as a base station for monitoring other monitoring devices.

Here, the monitoring devices can be designed so that they can be worn on the body and/or on the equipment of a person.

In order to achieve a flexible interface between the person and the monitoring device, the latter comprises at least one display, at least one operating element, at least one light emitting diode, at least one acoustic sensor and/or at least one loudspeaker.

Furthermore, an embodiment comprises at least one integrated internal sensor means (sensor mechanism, sensor device) and/or at least one connected external sensor means for capturing at least one physiological parameter of the wearing person, for capturing the fill level of a breathing gas container, of a parameter from the surroundings of the person, of a GPS device for determining the position of the wearing person and/or of a gas sensor for capturing hazardous gases in the surroundings of the person. Using one or more of these parameters, a risk evaluation of the deployment of the person is possible. In particular, it is also possible to receive and/or process data via the monitoring device from sensor means, which is arranged outside of the housing of the monitoring device; external sensor means are used. The data can be received and evaluated in particular by the monitoring device in the "base station mode."

Furthermore, an embodiment of a monitoring device can comprise a camera device, in particular a thermal imaging camera. A camera device, which is carried, for example, by the person can provide valuable information concerning the deployment events, which can be received and evaluated, for example, by the monitoring device in the "base station mode." By means of a thermal image camera it is possible, for example, to search for persons if the visibility at a deployment site is limited.

In an embodiment, a monitoring device comprises a means, mechanism or process for automatically setting the "basic mode" during the startup, in particular by coupling via physical proximity or a physical contact (for example, so-called bumping) with a monitoring device in the "base station mode." The physical proximity or the physical contact ensures that near-field communication makes possible a so-called pairing between the monitoring devices. In this manner, for example, during deployment, one monitoring device as base station, can be rapidly selected from several monitoring devices (that are of substantially identical design, for example), while the other monitoring devices are declared to be monitoring devices in the "basic mode." Alternatively, a switching means or mechanism for manually setting the operating mode is provided.

It is also advantageous for the monitoring device to comprise a water-tight and/or impact-resistant housing.

For a person who has been deployed, the data and/or signals captured by the monitoring device can be of immediate significance. Therefore, in an embodiment, it is possible to display, on a heads-up display of the person and/or in a respirator mask of the person, data depending on measured values of the acceleration sensor and/or at least one sensor. The data transfer from the monitoring device to the heads-up display or the respirator mask can occur wirelessly.

Furthermore, it can be advantageous if a connection means or mechanism, particularly a wireless one, works together with a respiratory protection apparatus in such a manner that the monitoring device can be connected automatically to the respiratory protection apparatus by activation of the respiratory protection apparatus. In the process, the monitoring device can, in particular, be automatically switched to the "basic mode."

Another problem is solved by a monitoring system with at least two compatible monitoring devices according to one of claims 1 to 13, wherein the "base station mode" is set in at least a first monitoring device, and the "basic mode" is set in at least one second monitoring device. In a particularly simple and economic design the compatible monitoring devices are substantially of identical design.

Figure 1:
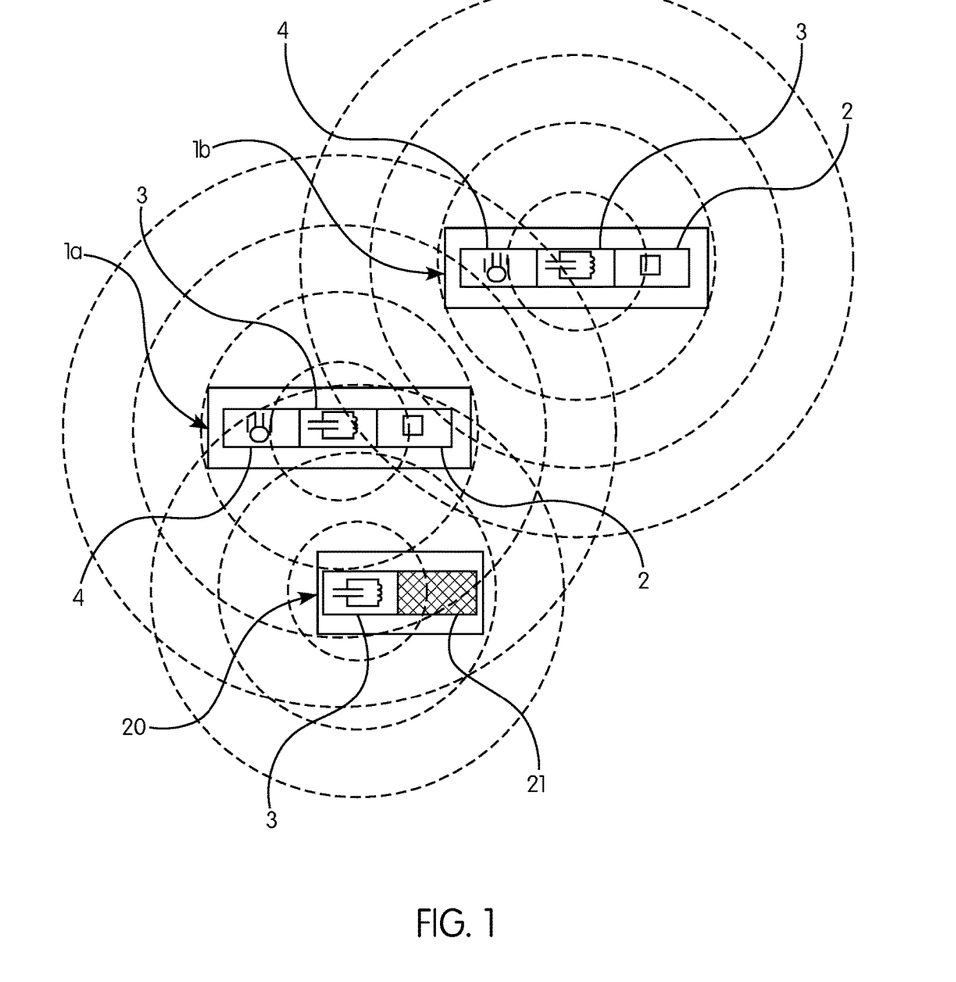
FIG. 1 is a schematic view of three monitoring devices which form a monitoring system according to the principles of the present invention.

In FIG. 1, a situation is diagrammatically represented in which the two monitoring devices 1a, 1b mutually exchange data and/or signals. Furthermore, an external sensor 20 (provided with a sensor 21 and a transmitter and receiver unit 3) is also represented, which exchanges data and/or signals with a monitoring device 1a. The monitoring devices 1a, 1b (optionally together with the external sensor 20 and internal sensor that are not shown here) thus form an embodiment of a monitoring system.

The data and/or signal exchange between the monitoring devices 1a, 1b is/are represented by the concentric circles, which symbolize the electromagnetic waves (for example, in radio, WLAN and/or another wireless data or signal transmission) used for the data and/or signal exchange. Below, it is assumed that the monitoring devices 1a, 1b are of substantially identical or in any case mutually compatible design.

The first monitoring device 1a, in the represented embodiment, is in the "basic mode," and the second monitoring device 1b is in the "base station mode."

The monitoring devices 1a, 1b can be worn by a person not represented in FIG. 1, in particular in the form of a hand-held apparatus or of an apparatus that can be attached to the equipment or clothing of the person. The monitoring devices 1a, 1b can be worn, for example, on a holder 10 suspended from the clothing of the person.

The housings of the monitoring devices 1a, 1b have a water-tight and impact-resistant design. The housings can be produced, for example, from plastic, composite materials or metal. It is preferable for the housings to meet the requirements of explosion protection.

The represented embodiments of the monitoring devices 1a, 1b in each case comprise three units: a data processing unit 2, a transmitter and receiver unit 3, and an acceleration sensor 4.

The acceleration sensor 4 detects movements in all three spatial directions and rotations about the three spatial axes, so that both steps taken by the person and also the change in the orientation of the monitoring device 1a, 1b in space are detected. In alternative embodiments, the acceleration sensor 4 can also detect fewer than these six motions. The motions of a monitored person, in particular sudden changes in the motion pattern of the monitored person, can contribute to monitoring the risk to which the person is exposed, among other things. Thus, using the acceleration sensor 4, it would be easy to detect, for example, loss of consciousness of the person to be monitored. As a safety device, an emergency button 9 can be used, which is pushed by the person to be monitored in an emergency. Alternatively, the emergency button 9 can be designed as a dead-man's button, so that failure to push the alarm button within a predetermined time period leads to triggering an alarm.

The data measured by the acceleration sensor 4, among other data, converge in the data processing unit 2. However, the data processing unit 2 also processes data captured by external sensor 20 and/or internal sensor (not represented in FIG. 1) and captured by the monitoring device 1a via the transmitter and receiver unit 3. It is also possible to capture via the transmitter and receiver unit 3 signals and/or data from other monitoring devices 1a (of a different design or of substantially the same design), which are then processed in the data processing unit 2.

Here it can be useful—depending on the intended use—to use sensor 20 with different sensors 21 within and/or outside of the monitoring device 1a, 1b.

Below, several sensors 20 (see also FIG. 3) are discussed, wherein the sensors can in principle also be combined in any desired manner with one another and adapted to an intended use.

Using a pressure sensor, the pressure in a breathing gas container of the person to be monitored can be measured. The breathing air that is still available is an important parameter for estimating the risk to which the deployed person is exposed.

Using a thermometer, the environmental temperature and/or the body temperature of the person can be captured. These temperatures as well represent parameters that indicate risk situations.

By means of a microphone, sounds of the monitored person and/or also sounds from the surroundings of the person can be captured. In the case of a person who has lost consciousness, the capturing of breathing sounds can be an important source of information in evaluating the risk situation.

A camera in the sensor 20 can be used to display to third parties the on-site deployment situation. A thermal image camera can be used to evaluate fires and/or the site of a fire and in order to locate persons in zones of limited visibility due to smoke, for example.

Data of a GPS unit can also be captured by the monitoring device 1a, 1b in order to determine the location of the monitored person.

A pulse oximetry sensor can provide valuable information on the physical capacity of the person to be monitored.

Gas sensors for hazardous gases (for example, explosive gases, toxic gases, $CO_2$) can also send their data to the monitoring device 1a, 1b.

For pressures, temperatures or other measured variables, the data processing device 2 can capture limit values and/or suspicious temporal changes in the measured variables, which can be useful for a risk evaluation. The data can also be displayed in the context of a heads-up display in a respirator mask. Thus, the wearing person of the display device 1a, 1b has selected values (for example, the fill state of the respiratory protection tank) within his/her view field during the deployment.

With one or more of these sensors 20, the monitoring device 1a, 1b is capable of monitoring a very wide variety of parameters on the equipment and in the surroundings of the person, and storing these data, such as, for example, temperatures, thermal images, live images, sounds, images of the surroundings, the gas composition of the environment, the pressure in the breathing air bottle of the monitored person, the position of the monitored person and physiological values of the person.

Here, the monitoring devices 1a, 1b have two modes: a "basic mode" G and a "base station mode" B.

In the "basic mode" G, the monitoring device 1a monitors, with the help of the data processing unit 2, the measurement data of the motion sensor 4 and of all the connected sensor units 20.

These monitored measurement data are transmitted by the transmitter and receiver unit 3 to a connected monitoring device 1b in the "base station mode" B. Typically, the monitoring device 1b in the "base station mode" B will receive data and/or signals from more than one monitoring device 1a in the "basic mode" G.

The "base station mode" B is a special mode which puts a monitoring device in the position of being able to fulfill the function of a base station for other monitoring devices 1a.

In this manner, a monitoring device 1b can also form a base station for other monitoring devices 1a, so that a dedicated base station in the form of, for example, a PC or a tablet is no longer necessary. It is also possible for several monitoring devices 1b to be in the "base station mode" B. Here, it is advantageous for the monitoring devices 1a, 1b to be substantially of identical design or at least compatible with respect to one another. It is also possible for the monitoring device 1a in the "basic mode" G to send data and/or signals to other monitoring devices 1a which are also in the "basic mode" G.

At the time of the startup, it is established for each monitoring device which operating mode B, G it is to have. This can occur, for example, by having the monitoring devices 1a provided for the "basic mode" G sign on by physical contact (a so-called "bump") with the monitoring device 1b selected as base station. By near-field communication (for example, NFC, BLUETOOTH, ZIGBEE communication) between the respective monitoring devices 1a, 1b, the monitoring devices 1a in the "basic mode" G thus report to the base station. Alternatively, signing on can also occur, instead of by means of a physical contact, by approaching the apparatuses, i.e., by establishing a physical proximity.

In this manner, the monitoring devices in the "base station mode" B can monitor the respective persons to be monitored that are provided with a monitoring device in the "basic mode" G.

The monitoring device with several operating modes G, B, can thus take over the properties of a monitoring device or of a base station. As a result of this combination of features, the procurement and the maintenance of large and heavy base stations implemented as a PC, laptop or tablet become unnecessary. Moreover, the monitoring device also has an additional advantage due to increased flexibility, since both the monitored person and also the monitoring person in performing their tasks can use the monitoring device with several operating modes. Moreover, as a result of the smaller and lighter design of the monitoring device with several operating modes, in comparison to a base station that is implemented as a PC, laptop or tablet, the freedom of operation of the monitoring person is increased, since he/she thus has the hands free in order to perform other activities besides monitoring the monitored person.

Moreover, the monitoring device 1a, 1b comprises means or mechanisms that allow communication over spatial distances using voice radio and/or preprogrammed messages. For this purpose, a microphone, loudspeakers and/or display elements are appropriately provided.

When starting the monitoring device, it is also possible to automatically establish by means of an RFID tag an operating mode B, G. The RFID tag here is located, for example, in a respiratory apparatus in/or on a harness, so that the monitoring device 1a is switched automatically to the "basic mode" G if the person to be monitored puts on a respiratory apparatus.

During deployments that cover, for example, a larger area, the data and/or radio transmission can be difficult. Therefore, the monitoring device 1a, 1b can also have a repeater function, so that a monitoring device 1a, 1b can be put down in a targeted manner in an area of the deployment zone in order to pass data and/or signals from zones that are difficult to access. In this manner, data and/or signals can be transmitted from monitoring devices 1a, 1b via other monitoring devices 1a, 1b—that function as repeaters—to the base station (and back).

In addition, an embodiment of the monitoring device 1a, 1b can have a pager function, i.e., a monitoring device 1a, 1b can be switched to a pager mode. For example, if one of the monitored persons is at risk, due to insufficient pressure in his/her breathing air bottle, the monitoring device 1b in the "base station mode" triggers the pager function in the monitoring device 1a to put it in the "pager mode." This can include an acoustic and optical alarm. Moreover, via the monitoring device in the "pager mode," the person can receive orders via preprogrammed messages.

A monitoring device in the "pager mode" is not used for recording measured values but for signaling to a person who, for example, is moving away from the monitoring device 1a in the "base station mode." If this person receives a message through the pager, he/she can immediately proceed to the base station.

The emergency button 9 can also be used in multiple ways. On the one hand, a person with a monitoring device 1a in the "basic mode" G, during deployment, can convey a message to a base station. On the other hand, from a monitoring device 1b in the "base station mode" B, a message can be sent to several deployed persons with a monitoring device 1a in the "basic mode" G, for example, if an area of the deployment zone has to be evacuated rapidly.

Figure 2:
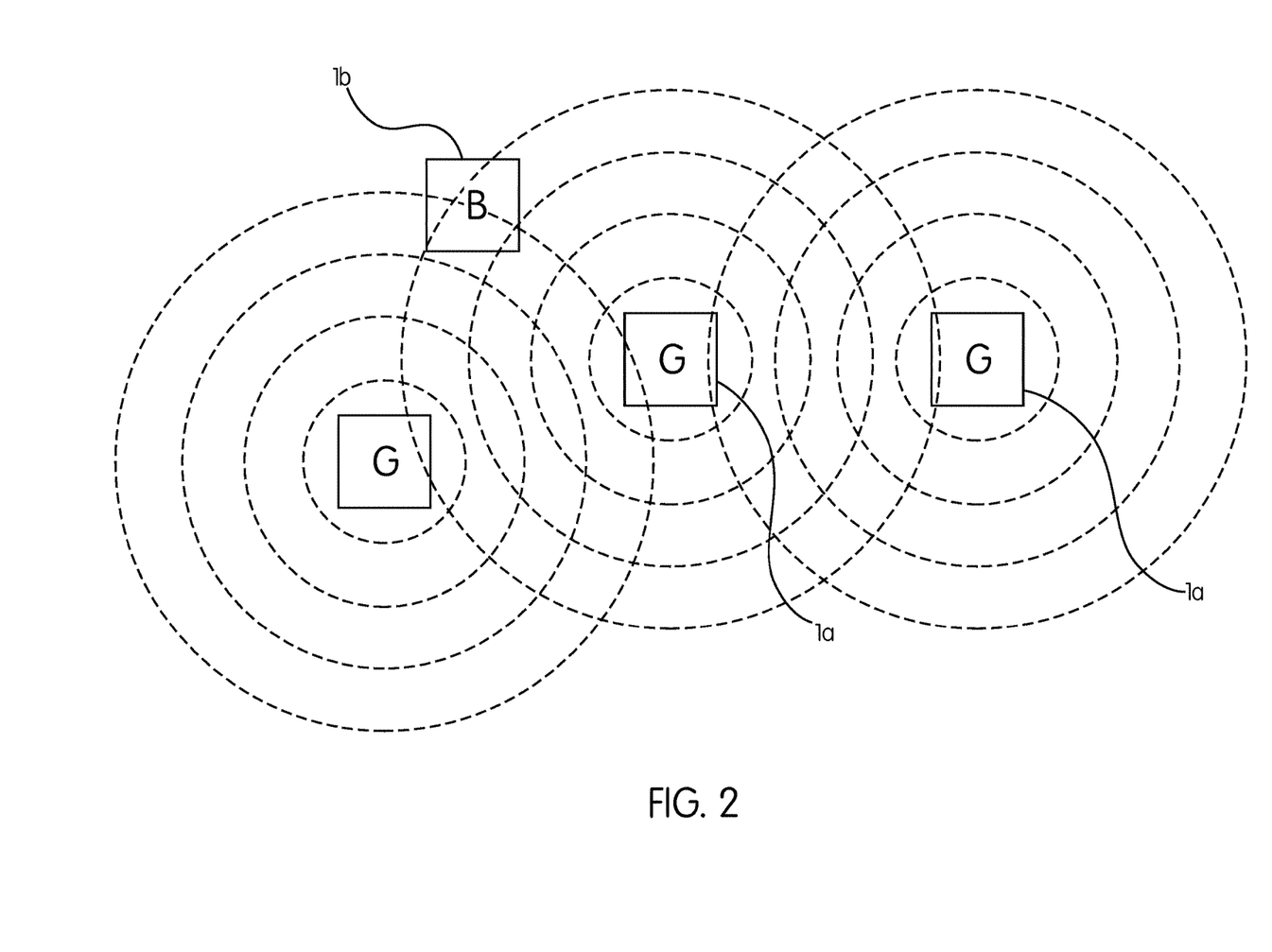
FIG. 2 is a schematic view of a monitoring system made of four monitoring devices of largely identical design according to the principles of the present invention.

In FIG. 2, a situation is represented in which three monitoring devices 1a in the "basic mode" G exchange data and/or signals with a monitoring device 1b in the "base station mode" B. Such an application can be useful if it is not possible to connect all the monitoring devices to a single monitoring device in the "base station mode" B. The four monitoring devices—of substantially identical design—thus form a monitoring system. Here, the monitoring devices are connected to one another directly or indirectly via the repeater function. By means of the repeater function, a monitoring device receives data and/or signals from another monitoring device even though the radio signal of the original sender is not strong enough to reach the receiver. The monitoring device 1a located in the middle of FIG. 2 here fulfills the repeater function, in order to connect the monitoring device 1a on the right to the monitoring device 1b in the "base station mode" B.

Figure 3:
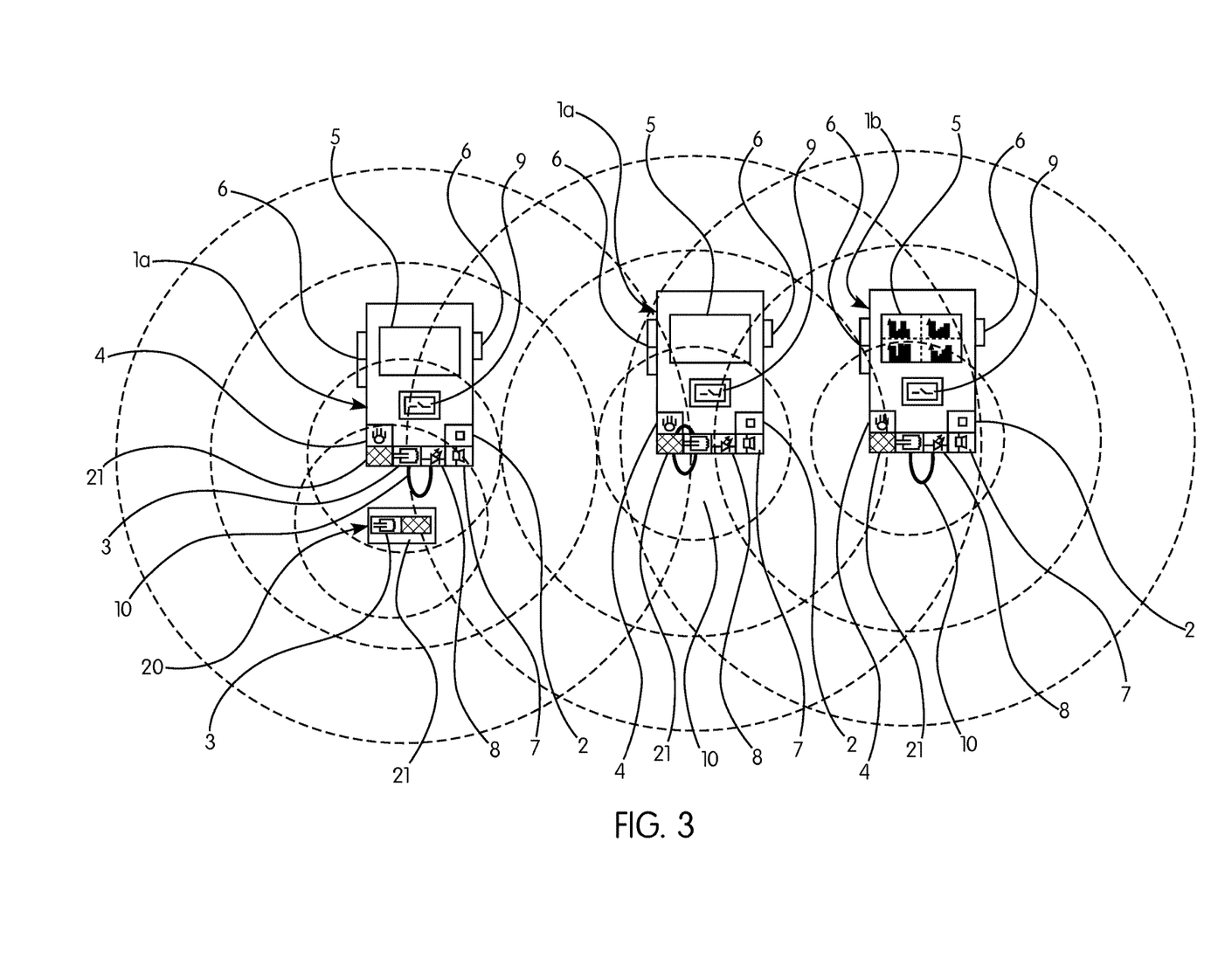
FIG. 3 is a schematic view of a monitoring system according to the principles of the present invention.

In FIG. 3, monitoring devices 1a, 1b are used in a similar manner as shown in FIG. 1, so that reference can be made to the corresponding description.

The monitoring devices 1a, 1b here each have a display 5, a light emitting diode 8 for indicating certain operating states, a loudspeaker 7 as well as operating elements 6.

The operating elements 6 and the display 5 make it possible, for example, for a monitored person, to transmit a pre-stored messages (for example, "injured person located," "new source of fire located," etc.) rapidly and simply using a monitoring device 1a in the "basic mode" G, from a monitoring device 1a to the base station.

The display 5 also shows measured values and data that are captured by the sensor 20. Here, using the operating elements 6, the user can select between different menus, such as "monitoring one's personal equipment" or "monitoring gas sensors," for example. Here, in each case several or all of the above-mentioned measurements can be used. The measured values (from internal and/or external sensors 20) and data are transmitted to the monitoring device 1b in the "base station mode" B.

In the "base station mode" B, the monitoring person can view on the display 5 all the measured values of all the monitored persons or have certain measured values displayed explicitly by using the operating elements 6. Furthermore, the person can use the operating elements 6 to select between prerecorded messages and send them to at least one monitored person.

The operating devices 1a, 1b each have an emergency button 9, by means of which an emergency call can be placed, without necessarily requiring any additional entries. The monitoring devices 1a, 1b also each have holders 10 by means of which they can be attached to the protective clothing of the person.

The monitoring devices 1a, 1b also have yet another function, where the current supply or control of the display 5 is connected to the acceleration sensor 4. This means that a signal of the acceleration sensor 4 is used to control the display 5. The display 5 is, for example, turned off automatically if the monitoring device 1a, 1b is suspended from the holder 10; suspension is registered by the accelerator sensor 4. The display 5 is automatically switched on again when the person picks up the monitoring device 1a, 1b again by hand in order to look at the display 5. This motion as well can be registered by the acceleration sensor. The connection between acceleration sensor 4 and display 5 can also be operated independently of other features of the described embodiments (for example, of the "basic mode" G and of the "base station mode" B).

Figure 4:
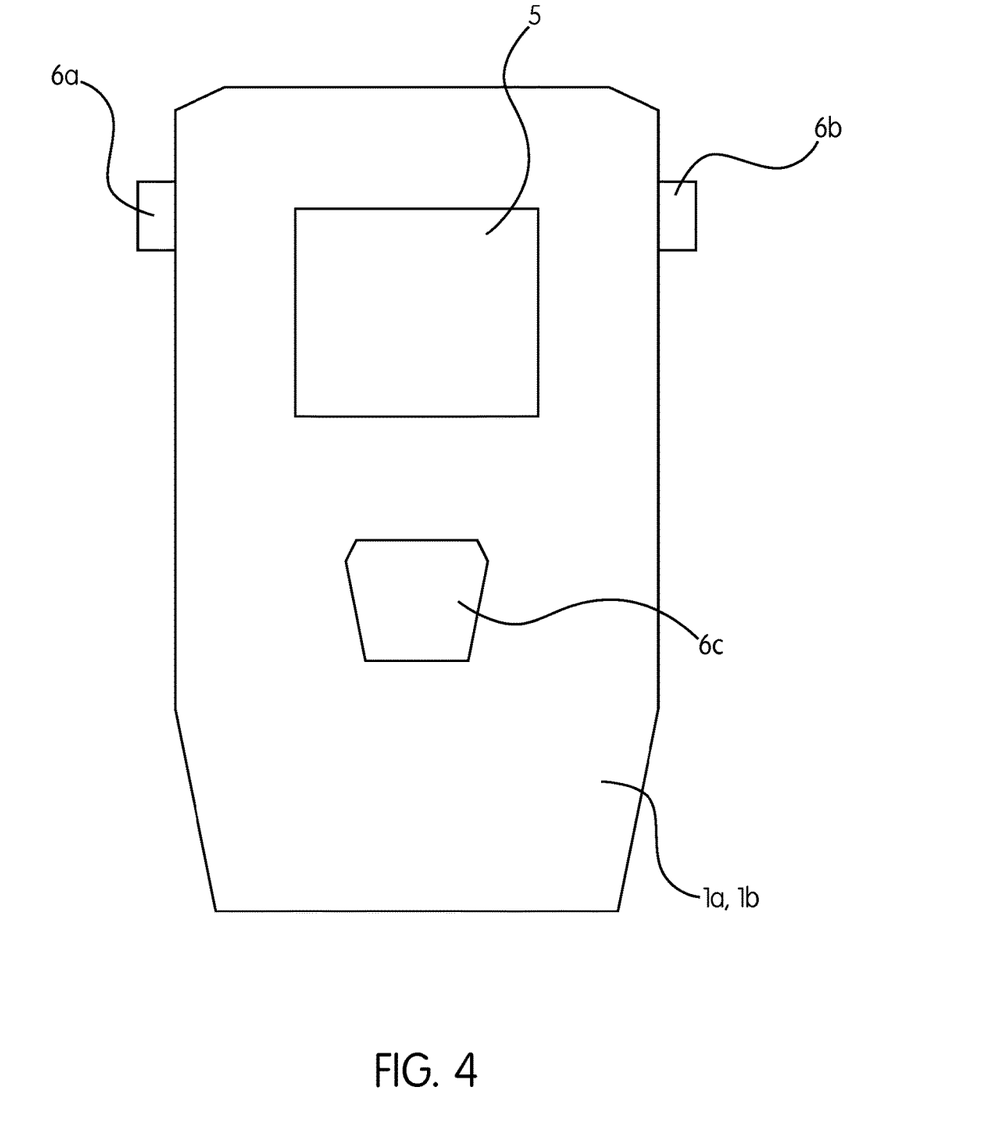
FIG. 4 is a schematic view of a monitoring device according to the principles of the present invention.

In FIG. 4, an embodiment of a monitoring device 1a, 1b is represented diagrammatically. This device has a simple and robust design. A graphic display or color display 5 allows the display of relevant data. A first operating element and a second operating element 6a, 6b allow the operation of the display, for example, the selection of a function or the switching to another screen on the display. A third operating element 6c is an alarm button for emergencies.

Below, several functional differences between the "basic mode" G and the "base station mode" B are described, as can be used in various embodiments. Here, it becomes clear that the monitoring devices 1a and 1b can be designed the same with respect to one another, but the programming in each case allows different functionalities to be selected. The differences here are described on the basis of the technical function groups in the monitoring devices 1a, 1b.

Motion Sensor 4:

"Basic mode" G: detection of motion of the person as well as a detection of the raising of the monitoring device 1a, 1b into the reading position.

"Base station mode" B: the motion sensor 4 here may have no function, since the monitoring devices 1a, 1b are operated generally in the stationary position.

Internal Data Memory:

"Basic mode" G: automatic data storage of essential parameters occurs, which the monitoring device 1a, 1b captures in the basic mode G.

"Base station mode" B: data storage of apparatus-specific parameters as well as event-based parameters from all the signed-on monitoring devices 1a, 1b in the "basic mode" G is carried out.

Display 5

"Basic mode" G: display of parameters of one's personal monitoring device 1a, 1b is provided. Two or more screens on one display 5 are possible so that it is possible to scroll between them. The layout of the display 5 is optimized accordingly.

"Base station mode" B: display of multiple parameters of the apparatus itself as well as display of transmitted parameters of the signed-on apparatuses is provided. There is a main screen and as many single screens as there are signed-on apparatuses. The layout of the display is optimized accordingly.

In the "basic mode" G, as in the "base station mode" B, it is possible to switch between the screens in the display using the operating element 6a, 6b. By means of a color background of the screens, it is possible to show the user that everything is in order (for example, breathing air supply sufficient, connection to base OK: green background, etc.), or a warning (for example, breathing air supply has fallen below a certain level, connection with the base is becoming worse, etc.): yellow background, or an alarm message (for example, breathing air supply below the warning level, connection lost, etc.): red background.

Operating elements 6 in an embodiment according to FIG. 4:

"Basic mode G": first and second operating element 6a, 6b for navigating on the display 4, as well as activation of "bumping" is provided. It is also possible to select special functions (for example, pairing with other monitoring devices, placing a message "deployment site reached"). The third operating element 6c is used as an alarm button 9 for emergencies.

"Base station mode" B: first and second operating element 6a, 6b for navigating on the display 5, in order, for example, to query the status of the individual signed-on monitoring devices 1a is provided. The third monitoring element 6c has the function of an alarm button and it is used for triggering an evacuation of all monitored the persons or of just one individual person.

Far-field radio module of the transmitter and receiver unit 3:

"Basic mode" G: activation of the software protocol for the monitoring device 1a in the "basic mode" G, when the monitoring device 1a is signed-on in the "base station mode" B, operates only one radio channel. The latter is used for the transmission of the apparatus-specific parameters.

"Base station mode" G: activation of the software protocol for the monitoring device 1b in the "base station mode" B manages the sign-on of new monitoring devices 1a, thus operating the channels of the signed-on monitoring devices 1a for querying and/or capturing the parameters.

Near-field communication (NFC) modules of the transmitter and receiver unit 3:

"Basic mode" G: NFC is used for reading in information of a monitoring device 1a and for "bumping" (P2P communication), i.e., for signing on with a monitoring device 1b in the "base station mode" B. Personalized data can also be read in and parameters can be set. NFC is switched on only if needed and it automatically switches off after a certain time.

"Base station mode" B: NFC is used for "bumping" (P2P communication), that is to say a monitoring device 1b can sign-on with a monitoring device 1b in the "base station mode" B. NFC automatically detects a monitoring device 1a in the "basic mode" G with activated NFC.

Data Processing Unit:

"Basic mode" G: the software represents the required functions and logic for the operation in the "basic mode" G. The same microprocessor is used with the same firmware as for the "base station mode" B.

"Base station mode" B: the software represents the required functions and logic for the operation in the "base station mode" B. The same microprocessor is used with the same firmware as for the "basic mode" G.

Figure 5:
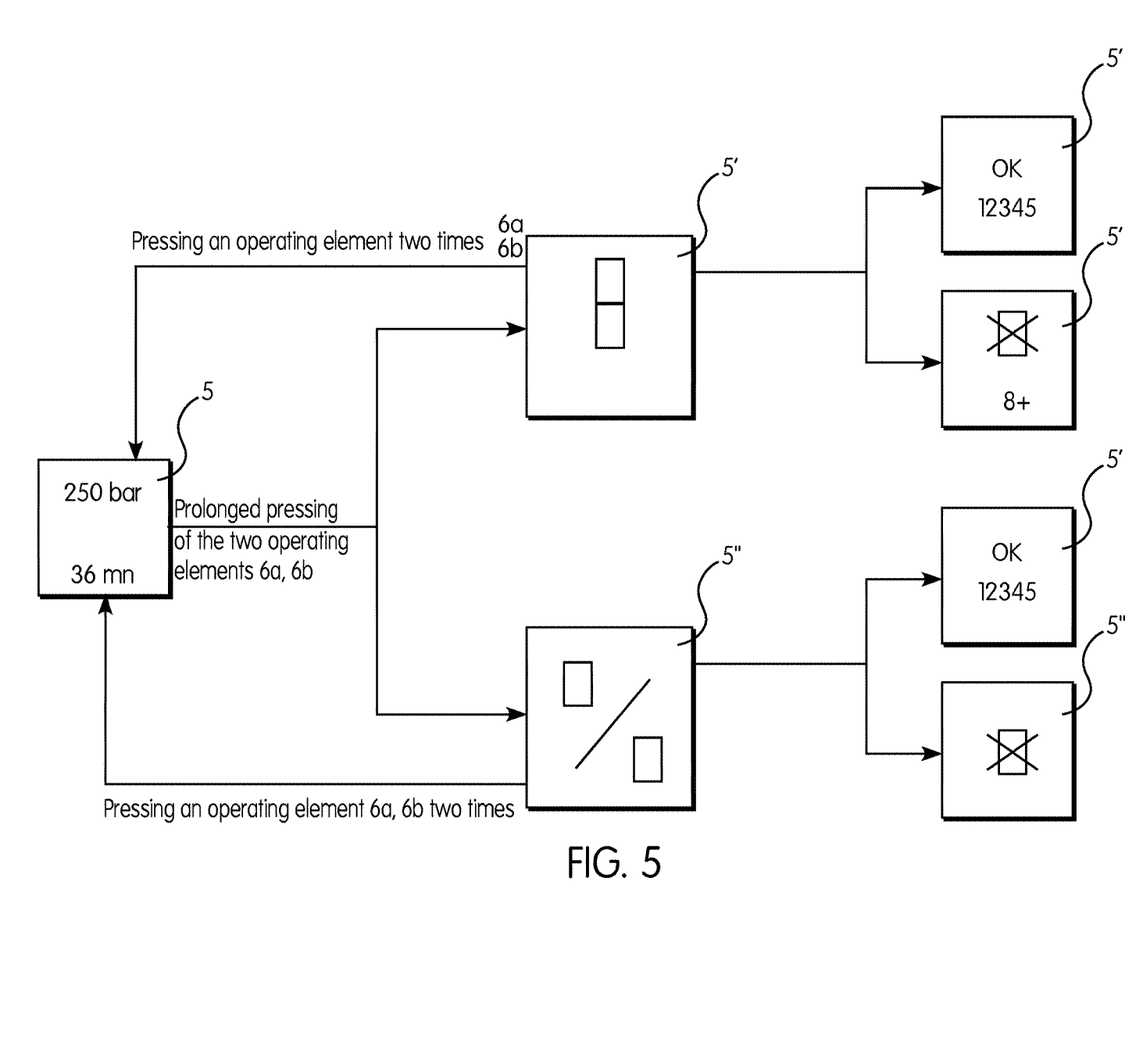
FIG. 5 is a schematic view of display views at the time of the establishment and disengagement of a data connection between transmission devices according to the principles of the present invention.

In FIG. 5, a diagrammatic representation is provided showing how a pairing occurs by physical contact (bumping) between a monitoring device 1a in the "basic mode" G and a monitoring device 1b in the "base station mode" B, wherein diagrammatic views are represented on the displays 5', 5". In addition to the sign-on, that is the bumping (display view 5'), the sign-off (debumping; display view 5") between the monitoring devices 1a, 1b is also represented. Display views here relate to a monitoring device 1a in the "basic mode" G.

The two display views 5', 5" replace the main view of the display 5 on which the current pressure of the pressurized container of the respiratory protection apparatus and the remaining deployment time are represented. In other operating situations, the main view can also contain other data.

The arrows in FIG. 5 show how a user can switch between the individual views or what is displayed as a result of an operating action.

When a monitoring device 1a is in the "basic mode" G, it can be "paired" with a monitoring device 1b in the "base station mode" B. If, for example, in the embodiment of FIG. 4, the two operating elements 6a, 6b are pressed at the same time, a bumping is initiated, if there is physical contact between the monitoring devices 1a, 1b.

If the pairing already exists between the monitoring devices 1a, 1b, then prolonged pressing of the two operating elements leads to a disengagement of the data connection (debumping).

In both cases, by pressing one of the operating elements 6a, 6b twice, the user reaches the main view of the display 5. Alternatively, this can also occur automatically after a timeout.

If a bumping has been carried out, then there are, for example, two view possibilities on the display. When the connection between the monitoring devices 1a, 1b has been established successfully, an "OK" and a check number (ID of the base station) are displayed. When all the places are already occupied on the monitoring device 1a in the "base station mode" B—in the present case eight places are displayed, then this is represented accordingly on the display 5'. In that case, a sign-on to another monitoring device 1b in the "base station mode" B should take place.

If the debumping was successful, this is also displayed on the display 5'. If the debumping was not successful, for example, because it took place on the incorrect monitoring device, this is displayed on the display 5".

In each case, after a timeout (for example, 3 seconds), there is an automatic switch to the main view of the display 5.

Figure 6:
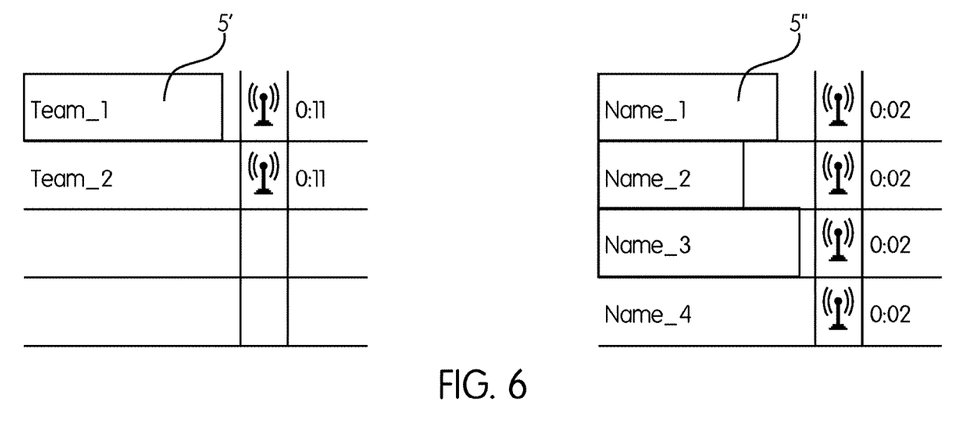
FIG. 6 is a schematic view of two display views in the base station mode in a first embodiment according to the principles of the present invention.

In FIG. 6, two display views 5', 5" of a monitoring device 1b in the "base station mode" B are represented. In a first view 5' (team view), two teams are represented with their different names (first column). In the second column, a representation is given showing that the data connection to all the teams is good. In the third column, a representation is given showing that in both teams the team member with the lowest breathing air supply still has 11 minutes of time left. By an appropriate selection, the user can send an evacuation message to individual teams or to all the teams.

In the second display view 5", the individual team members are represented, wherein the team assignment is indicated, for example, using a color background. By selection, an evacuation message can be sent to individual team members or to several team members.

Figure 7:
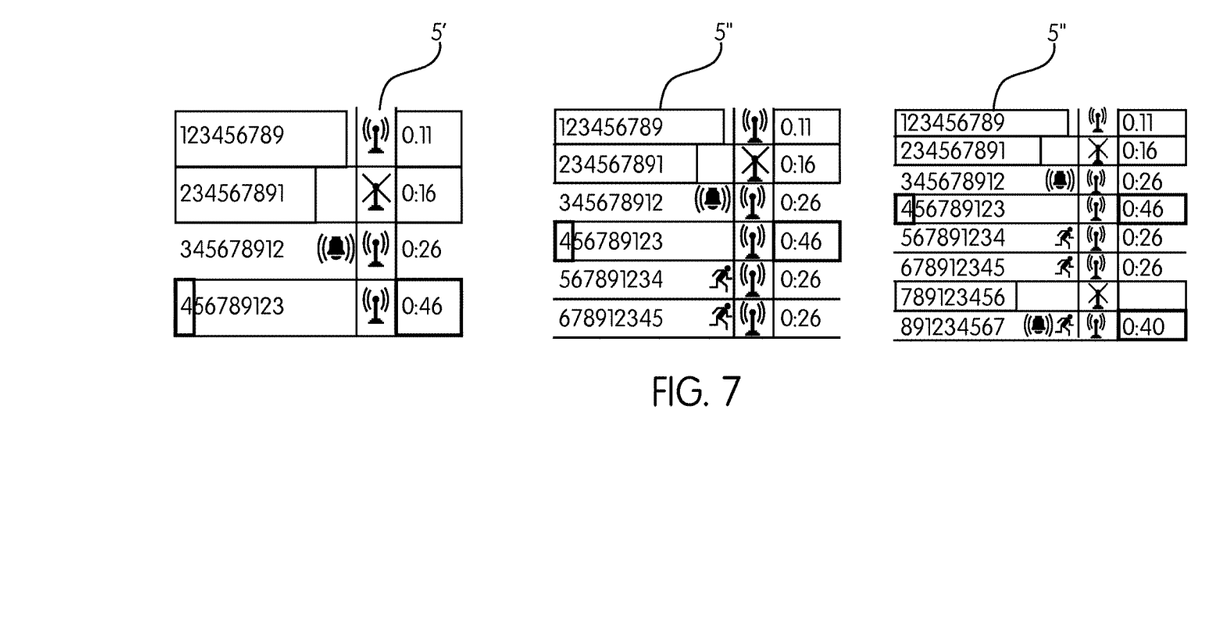
FIG. 7 is a schematic view of two display views in the base station mode in a second embodiment according to the principles of the present invention.

In FIG. 7, three display views 5', 5", 5"' of an additional embodiment of a monitoring device 1b in the "base station mode" B are represented. Here, all at once, four (5'), six (5') and eight (5"') connected monitoring devices 1a in the "basic mode" are represented. Here the user identifiers, the alarm states, the respective status of the radio connection, possible evacuation, the pressure values and/or deployment times can be represented.

Figure 8:
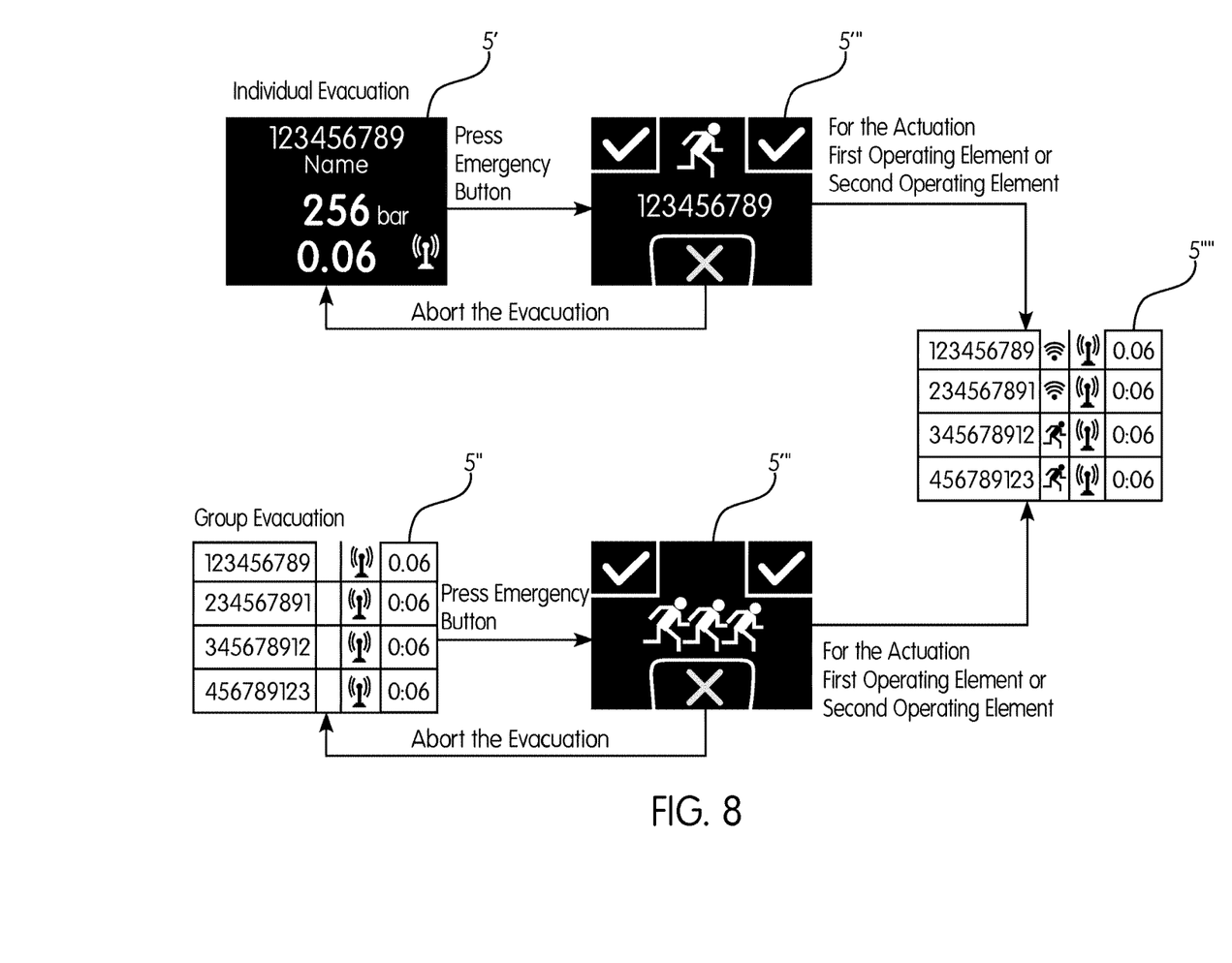
FIG. 8 is a schematic view of evacuation orders according to the principles of the present invention.

In FIG. 8, different display views 5', 5" are represented, showing an individual evacuation (5') and a group evacuation (5").

In the case of the individual evacuation, the starting point is a display view 5' for an individual monitoring device 1a in the "basic mode" G. The display view 5' shows that the apparatus with ID 123456789 has a deployment time of 6 minutes and that the connection with the monitoring device 1b in the "base station mode" B is satisfactory. If the emergency button 9 is pressed, then an evacuation signal is prepared for the corresponding monitoring device 1a. In the display view 5'" it is shown that, before sending the evacuation signal, an actuation by means of one of the two operating elements 6a, 6b is required. Alternatively, the evacuation can be aborted by pressing the emergency button 9 again.

In an additional display view 5"" it is shown that the evacuation signal has been sent to the monitoring device 123456789. For an additional monitoring device 234567891, an evacuation signal has also been issued. For two additional monitoring devices 345678912 and 456789123, the evacuation orders have already been confirmed, which is represented symbolically using the symbol of a "running human."

In the case of a group evacuation order (see display view 5″) for four monitoring devices 1a, an evacuation order is transmitted to all the monitoring devices 1a represented on the display. As in the individual evacuation, a confirmation must occur here as well (see display view 5′″). Subsequently, a display view 5″″ is shown, which has already been shown in connection with the individual evacuation.

It should be understood that the display views 5′, 5″, 5′″, 5″″ represented here are merely examples and that other representation forms or procedures can also be selected.

This disclosure has been presented for purposes of illustration and description but is not intended to be exhaustive or limiting. Many modifications and variations will be apparent to those of ordinary skill in the art. The embodiments were chosen and described in order to explain principles and practical application, and to enable others of ordinary skill in the art to understand the disclosure for various embodiments with various modifications as are suited to the particular use contemplated.

Although illustrative embodiments of the invention have been described herein with reference to the accompanying drawings, it is to be understood that the embodiments of the invention are not limited to those precise embodiments, and that various other changes and modifications may be affected therein by one skilled in the art without departing from the scope or spirit of the disclosure.

LIST OF REFERENCE NUMERALS

1a Monitoring device in the "basic mode"
1b Monitoring device in the "base station mode"
2 Data processing unit
3 Transmitter and receiver unit
4 Acceleration sensor
5 Display
5′, 5″, 5′″, 5″″ Display views
6 Operating elements
7 Loudspeaker, acoustic sensor
8 LED
9 Emergency button/dead-man's button/evacuation button
10 Holder
20 Sensor
21 Sensor
B Base station mode
G Basic mode

The invention claimed is:

1. A mobile monitoring device, comprising:
at least one transmitter;
at least one receiver;
at least one sensor for recording measured values on or in at least one of the following: a wearing person, a surrounding of the wearing person, equipment of the wearing person, or any combination thereof;
at least one processing unit in operative connection with the at least one transmitter, the at least one receiver, and the at least one sensor;
wherein the at least one processing unit sets the mobile monitoring device to one of a basic mode and a base station mode according to a setting;
wherein, in the basic mode, the at least one processing unit is configured to monitor the measured values of the at least one sensor,
wherein, in the base station mode, the at least one processing unit is configured to monitor measured values of at least one other, compatible mobile monitoring device operating in the basic mode, and
wherein the at least one processing unit is configured to automatically set the mobile monitoring device to the basic mode at a time of start up by coupling, via physical proximity to or physical contact with, a compatible mobile monitoring device set to the base station mode.

2. The mobile monitoring device of claim 1, wherein the mobile monitoring device uses the at least one sensor to monitor at least one physiological characteristic of a wearing person and at least one ambient characteristic when in the basic mode.

3. The mobile monitoring device of claim 1, wherein the mobile monitoring device receives data from at least one other, compatible mobile monitoring device when in the base station mode.

4. The mobile monitoring device of claim 1, further comprising a connection device, wherein the basic mode is set when a respiratory protection apparatus is connected to the mobile monitoring device via the connection device.

5. The mobile monitoring device of claim 4, wherein the connecting device includes near field communication.

6. The mobile monitoring device of claim 1, wherein the at least one transmitter and the at least one receiver are configured as a communication system comprising at least one of the following: a bidirectional communication unit, a pager system, a repeater system, or any combination thereof.

7. The mobile monitoring device of claim 1, wherein the at least one sensor comprises at least one of the following: a connection device for an external sensor, an integrated sensor, or any combination thereof.

8. The mobile monitoring device of claim 1, wherein the at least one sensor monitors a characteristic comprising at least one of the following: at least one physiological parameter of a wearing person, a quantity of remaining breathable air in a container, an environmental parameter, a relative location, or any combination thereof.

9. The mobile monitoring device of claim 1, further comprising a camera.

10. The mobile monitoring device of claim 9, wherein the camera is a thermal imaging camera.

11. The mobile monitoring device of claim 1, further comprising a display, wherein display brightness is based at least partially on the set mode of operation.

12. The mobile monitoring device of claim 1, wherein, in the base station mode, measured values of the at least one sensor are processed by the at least one other, compatible mobile monitoring device.

13. The mobile monitoring device of claim 1, further comprising at least one attachment arrangement configured to facilitate attachment of the device to a person.

14. The mobile monitoring device of claim 1, further comprising at least one of the following: at least one display, at least one operative element, at least one light emitting diode, at least one acoustic signal emitter, at least one loudspeaker, or any combination thereof.

15. The mobile monitoring device of claim 1, further comprising at least one housing configured to be at least one of the following: water-tight, impact-resistant, or any combination thereof.

16. The mobile monitoring device of claim 1, further comprising a display,
wherein the at least one sensor comprises at least one acceleration sensor; and wherein the display is switchable between on and off states by a signal of the at least one acceleration sensor.

17. A monitoring system, comprising:
a plurality of mobile monitoring devices;
one of the plurality of mobile monitoring devices being set to a base station mode;
each remaining device of the plurality of mobile monitoring devices being set to a basic mode;
the one of the plurality of mobile monitoring devices set to the base station mode receiving data from and issuing commands to each remaining device of the plurality of mobile monitoring devices set to the basic mode;
wherein each remaining device of the plurality of mobile monitoring devices is configurable to be set to the base station mode;
wherein the one of the plurality of mobile monitoring devices set to the base station mode is configured to be set to the basic mode after being set to the base station mode; and
wherein each of the plurality of mobile monitoring devices is configured to be automatically set to the basic mode at a time of start up by coupling, via physical proximity to or physical contact with, the one of the plurality of mobile monitoring devices set to the base station mode.

18. The monitoring system of claim 17, wherein each of the plurality of mobile monitoring devices comprises:
at least one acceleration sensor; and
a display switchable between on and off states by a signal of the at least one acceleration sensor.

* * * * *